United States Patent [19]

Watanabe et al.

[11] Patent Number: 4,831,265
[45] Date of Patent: May 16, 1989

[54] METHOD OF PRODUCING QUINONE DERIVATIVES

[75] Inventors: Masazumi Watanabe, Kawanishi; Isuke Imada, Izumi, both of Japan

[73] Assignee: Takeda Chemical Industries, Ltd., Osaka, Japan

[21] Appl. No.: 33,864

[22] Filed: Apr. 3, 1987

Related U.S. Application Data

[63] Continuation of Ser. No. 347,271, Feb. 9, 1982, abandoned.

[30] Foreign Application Priority Data

Feb. 9, 1981 [JP] Japan ................................ 56-18319

[51] Int. Cl.$^4$ ...................... C07C 50/26; C07C 50/00
[52] U.S. Cl. .................................. 260/396 R; 549/416
[58] Field of Search ..................... 260/396 R; 549/416

[56] References Cited

U.S. PATENT DOCUMENTS

| | | | |
|---|---|---|---|
| 2,398,418 | 4/1946 | Fieser | 260/396 R |
| 2,553,648 | 5/1951 | Fieser | 260/396 R |
| 4,139,545 | 2/1979 | Morimoto et al. | 260/396 R |

FOREIGN PATENT DOCUMENTS 140943  11/1981  Japan .............................. 260/396 R

OTHER PUBLICATIONS

Lin et al., Journal of Medicinal Chemistry, 1974, vol. 17, No. 7, pp. 668–671.

Primary Examiner—Werren B. Lone
Attorney, Agent, or Firm—Wenderoth, Lind & Ponack

[57] ABSTRACT

A quinone compound of the formula:

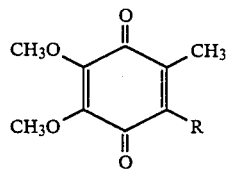

wherein R stands for an alkyl group of 1 to 22 carbon atoms having at its terminal end a hydroxyl group which may be protected, can be obtained with industrial advantage by allowing a compound of the formula:

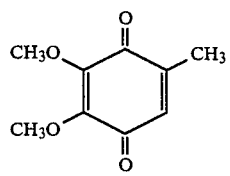

to react with a peroxide of a carboxylic acid of the formula:

RCOOH wherein R is as defined above, or with a peroxide of an acid anhydride of the carboxylic acid. The quinone compound wherein R stands for an alkyl group of 1 to 2 carbon atoms having at its terminal end an optionally protected hydroxyl group, is a novel compound and has antifibrotic activity.

3 Claims, No Drawings

METHOD OF PRODUCING QUINONE DERIVATIVES

This application is a continuation of now abandoned application Ser. No. 347,271, filed Feb. 9, 1982.

This invention relates to an industrially advantageous novel method of preparing quinones which are useful as medicines.

Quinones of the general formula (I):

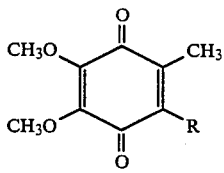

wherein R stands for an alkyl group of 1 to 22 carbon atoms having at its terminal end an optionally protected hydroxy group, are useful for abating myocardosis and cerebral disturbance, and are effective, for example, for reactivating histological metabolism in ischemic- and congestive-cardiac insufficiency and cerebral circulation disturbance in animals including human beings.

As a method of preparing the compound of the above general formula (I), the one disclosed by U.S. Pat. No. 4,139,545 has been known. But, this method requires many reaction steps and is hardly regarded as an industrially advantageous one.

Under the technical background as above, the present inventors have conducted extensive studies, and reached the finding that the desired compound (I) can be prepared in one single step from a compound of the formula (III):

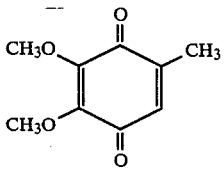

by using a peroxide of a carboxylic acid of by the formula:

RCOOH     (II)

wherein R stands for an alkyl group having at its terminal end an optionally protected hydroxyl group, or a peroxide of an acid anhydride of the carboxylic acid (II).

In short, this invention relates to a method of preparing quinones of the general formula (I), characterized by allowing a compound of the formula (III) to react with a peroxide of a carboxylic acid the formula (II) or with a peroxide of an acid anhydride of the carboxylic acid.

In the general formulas (I) and (II), R stands for an alkyl group having 1 to 22 carbon atoms and having at its terminal end an optionally protected hydroxyl group, and, as the alkyl group, there may be exemplified, among others, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicocyl heneicocyl or docoyl. Among them, straight-chained alkyls are preferable.

When the hydroxyl groups at the terminal end of these alkyl groups are protected, the protective groups may be exemplified by alkyl groups having 1 to 4 carbon atoms such as methyl, ethyl, n-propyl, i-propyl, n-butyl, i-butyl, t-butyl, etc. aliphatic carboxylic acyl groups having 1 to 4 carbon atoms such as formyl, acetyl, propionyl or butyryl, aromatic acyl group having 7 to 8 carbon atoms such as phenyl acetyl, and a, tetrahydropyranyl group.

The method of this invention is conducted by allowing a compound (III) to react with a peroxide of compound (II) or with a peroxide of an acid anhydride of the carboxylic acid. [The "acid anhydride" is hereinafter sometimes referred to as "compound (II')"]. The peroxide of compound (II) is shown by the formula:

RCOOOH     (IV')

The peroxide of an acid anhydride of the carboxylic acid (II) is shown by the formula:

(RCOO)₂     (IV'')

[The peroxides (IV') and (IV'') are hereinafter sometimes referred to as "peroxide (IV)"] As the peroxide (IV), any compound may be used so long as it gives rise to an alkyl radical with the release of carbon dioxide gas by heating. The peroxide (IV) can be obtained by allowing a peroxide such as hydrogen peroxide, its metal salt (e.g. $Na_2O_2$, $K_2O_2$, $Li_2O_2$, etc.) or lead tetracetate to react with, for example, carboxylic acid (II), its halogenide or acid anhydride (II').

The reaction of this invention is preferably conducted in an appropriate inert organic solvent such as n-hexane, ligroin, toluene, xylene or propionic acid. The amount of the peroxide (IV) to be brought into contact with the compound (II) is usually in the range of 1 to 2 moles per mole of compound (II). The reaction temperature is within the range of about 50° C. to 150° C., preferably about 80° C. to 100° C., and the reaction time is preferably about 0.5 to 3 hours. The reaction of this invention proceeds, along with generation of carbon dioxide gas, under remarkably mild conditions, with little side reactions, to give the desired product in a high yield, and unreacted materials can be recovered without substantial loss.

The reaction of this invention may be conducted under such conditions as producing a peroxide (IV) in the reaction system. For example, the reaction is conducted by allowing a compound (III) to react with a compound (II) or its acid anhydride (II') in the presence of a tetra-valent lead compound (e.g. lead tetracetate). The reaction is preferably conducted in an appropriate inert solvent (e.g. n-hexane, ligroin, toluene, xylene, acetic acid, propionic acid, etc.), and the reaction temperature is within the range of about 50° C. to about 150° C., preferably about 80° C. to about 100° C.

In case where the R of a compound (I) prepared by the method of this invention has unprotected hydroxyl groups at its terminal end, a compound having protected hydroxyl groups at the terminal end of its alkyl group can be obtained upon necessity by subjecting the unprotected hydroxyl groups to acylation or alkylation. The acylation is conducted by allowing carboxylic acid or a reactive derivative thereof at its carboxyl group (e.g. carboxylic anhydride, carboxylic halide, carboxylic lower alcohol ester, etc.) to react with the compound (I) as above, in the presence or absence of a mineral acid such as sulfuric acid or hydrochloric acid; an organic acid such as aromatic sulfonic acid; a Lewis acid such as fluorinated boron etherate; acid ion-exchange resin; or a dehydrating agent such as anhydrous magnesium sulfate, molecular-sieve or dicyclohexylcarbodiimide.

The alkylation is conducted by allowing a halogenated alkyl to react with the compound (I) as above in the presence of a base (e.g. sodium amide, potassium carbonate, triethylamine, sodium hydroxide, barium oxide, silver oxide, sodium hydride, etc.).

In case where the hydroxyl group at the terminal end of R of the quinones (I) is protected with an carboxylic acyl group, such quinones can be converted to those having an unprotected hydroxyl group at the terminal end of R by subjecting them to hydrolysis by per se conventional means. The hydrolysis is conveniently conducted in the presence of, for example, a mineral acid (e.g. sulfuric acid, hydrochloric acid, etc.), or an alkaline substance (e.g. sodium hydroxide, potassium hydroxide, calcium hydroxide, etc.). The compound (I) having an unprotected hydroxyl group at the terminal end of R can be prepared also by subjecting a quinone (I) whose R has protected hydroxyl at its terminal end to hydrolysis in the presence of a suitable antioxidant (e.g. pyrogallol, etc.) or a reducing agent (e.g. hydrosulfite, etc.) to give a compound of the general formula:

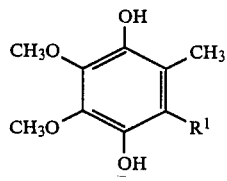

(V)

wherein $R^1$ stands for an alkyl group having an unprotected hydroxyl group at its terminal end, and by subjecting this compound to oxidation with, for example, ferric chloride, silver oxide, air, etc.

Thus-prepared quinones (I) can be easily recovered by a per se conventional means, e.g. pH change, phasic transfer, concentration, distillation under reduced pressure, chromatography, crystallization, recrystallization, etc.

Among the compounds (I) prepared by the present method, a compound of the formula:

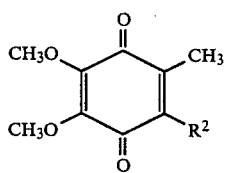

(VI)

wherein $R^2$ stands for an alkyl group having 1 to 2 carbon atoms and having at its terminal end an optionally protected hydroxyl group, is a novel compound and has antifibrotic activity. Antifibrotic substances having antifibrotic activity are possessed of protocollagen proline hydroxylase inhibitor activity, collagen biosynthesis inhibitor activity and other properties as well. Protocollagen proline hydroxylase is an enzyme which specifically hydroxylates the proline residue of the protocollagen synthesized by ribosome in animal cells and is one of the important rate-limiting factors in the biosynthesis of collagen. The compound (VI) can be successfully utilized for prophylaxis and treatment of diseases including various forms of organ fibrosis accompanied by an excess accumulation of collagen, such as arteriosclerosis, hepatic cirrhosis, keloid, scleroderma, sheumatic arthritis, pulmonary fibrosis, etc. in mammals including human beings. The compound (VI) may be orally administered in such dosage forms as tablets, capsules, powders, granules, etc. or by other routes in such forms as injections, suppositories, pellets and so on.

The dosage of the compound (VI) varies with the kind of diseases, symptoms, administration routes or dosage forms, but in case of parenteral administration such as injection, the daily dose as the compound (VI) is about 0.3 mg to 100 mg, preferably 1 mg to 30 mg for adult humans, and in case of oral administration, the daily dose is about 5 mg to 600 mg, preferably 10 mg to 300 mg for adult humans.

The compound (VI) can also be prepared by oxidizing a compound of the formula:

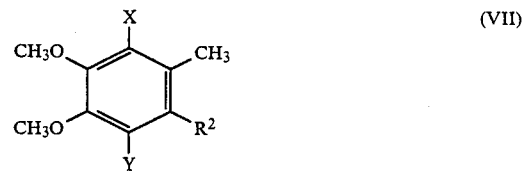

(VII)

wherein $R^2$ has the meaning given above, X is hydrogen or hydroxyl which may be protected and Y is hydroxyl which may be protected.

As to the formula (VII), the protective group for the hydroxyl X or Y may be any type of groups which can be easily removed and is exemplified by alkyl, aralkyl, acyl, acetal and silyl.

The alkyl for the protective group is advantageously those having up to 4 carbon atoms exemplified by methyl, ethyl, n-propyl, i-propyl, n-butyl and i-butyl. The aralkyl for the protective group is advantageously benzyl.

As the acyl for the protective group, there may be mentioned alkyl carbonyl, aryl carbonyl, aralkyl carbonyl, especially alkyl carbonyl having 1 to 4 carbon atoms such as acetyl, n-propionyl and n-butyryl. The acetal for the protective group is advantageously α-tetrahydropyranyl and methoxymethyl.

As the silyl for the protective group, trimethylsilyl is used advantageously.

The procedure for this oxidation may be any procedure by which phenol may be converted to quinone without affecting the hydroxyl. The oxidizing agent is advantageously ferric chloride, silver oxide, nitrosodisulfonate and so on.

This oxidation is generally conducted in a suitable solvent. Any solvent that does not interfere with this oxidation may be employed for this purpose; thus, for example, water, a dilute aqueous solution of an acid, or an alkali, acetone, ethanol, dioxane, ether, acetic acid dimethylformamide, tetrahydrofuran and so on may be mentioned.

While the reaction temperature and time are dependent to a certain extent upon the type of oxidizing agent, generally preferred conditios are about 0° to 25° C. and abot 0.5 to 5 hours.

The compound (VII) can be prepared by allowing a compound of the formula:

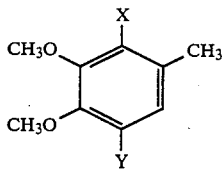

(VIII)

wherein X and Y have the same meaning as given above, to react with a peroxide of the compound $$R^2COOH \qquad (IX)$$

wherein $R^2$ has the same meaning as given above, or with a peroxide of an acid anhydride of the carboxylic acid (IX) by a manner similar to that of the reaction of the compound (III) with the compound (IV).

Example 1

To a solution of 250 mg of 2,3-dimethoxy-5-methyl-1,4-benzoquinone in 1.8 ml of toluene was added little by little 1.4 g of bis(11-acetoxyundecanoyl)peroxide under stirring at a temperature of 85°–90° C. The mixture was heated for two hours. The resultant was cooled and diluted with water, followed by extraction with ethylacetate. The extract was washed with water and dried over anhydrous sodium sulfate. The solvent was evaporated under reduced pressure. The residue was subjected to chromatography on silica-gel, followed by recrystallization from aqueous ethanol to yield 216 mg of 6-(10-acetoxydecyl)-2,3-dimethoxy-5-methyl-1,4-benzoquinone, m.p. 38° C. Simultaneously, 84 mg of the starting material, 2,3-dimethoxy-5-methyl-1,4-benzoquinone, was recovered.

In a mixture of 0.04 ml of concentrated hydrochloric acid and 11 ml of methanol was dissolved 216 mg of 6-(10-acetoxydecyl)-2,3-dimethoxy-5-methyl-1,4-benzoquinone, and the solution was left standing overnight at room temperature. The reaction solution was concentrated under reduced pressure and the concentrate was diluted with water, which was subjected to extraction with ethyl acetate. The extract was washed with a saturated aqueous solution of sodium chloride, then dried. The solvent was evaporated under reduced pressure. The residue was recrystallized from hexane-ethylacetate to yield 115 mg of 6-(10-hydroxydecyl)-2,3-dimethoxy-5-methyl-1,4-benzoquinone as orange-colored needles, m.p. 52°–53° C.

Example 2

In 2 ml of acetic acid was dissolved 0.36 g of 2,3-dimethoxy-5-methyl-1,4-benzoquinone. The solution was allowed to react in a manner similar to that of Example 1 with bis(acetoxyacetyl)peroxide prepared from 0.41 g of acetyl glycollic acid chloride. The reaction product was purified by means of chromatography on silica-gel to give 29 mg of 6-acetoxymethyl-2,3-dimethoxy-5-methyl-1,4-benzoquinone. NMR spectrum (δ value in CDCl$_3$): 2.07 (3H, s, CH$_3$), 2.12 (3H, s, COCH$_3$), 4.03 (6H, s, OCH$_3$), 5.00 (2H, s, CH$_2$)

In a similar manner to Example 1, 96 mg of 6-acetoxymethyl-2,3-dimethoxy-5-methyl-1,4-benzoquinone was subjected to hydrolysis, followed by recrystallization from hexane-ether to yield 29 mg of 6-hydroxymethyl-2,3-dimethoxy-5-methyl-1,4-benzoquinone, m.p. 52°–54° C.

Elemental Analysis for C$_{10}$H$_{12}$O$_5$: Calcd.: C, 56.60; H, 5.70; Found: C, 56.54; H, 5.71.

Example 3

By a similar manner to Example 2, 6-(2-hydroxyethyl)-2,3-dimethoxy-5-methyl-1,4-benzoquinone was obtained by using bis(β-acetoxypropanoyl)peroxide in place of bis(acetoxyacetyl)peroxide.

NMR spectrum (δ value in CDCl$_3$): 2.05 (3H, s, CH$_3$), 2.67 (2H, t, J=7 Hz, CH$_2$), 3.12 (1H, b.OH), 3.68 (2H, t, J=7 Hz, CH$_2$O), 3.95 (6H, s, CH$_3$O).

Elemental Analysis for C$_{11}$H$_{14}$O$_5$: Calcd.: C, 58.4; H, 6.24; Found: C, 58.51; H, 6.27.

Example 4

6-(2-Hydroxyethyl)-2,3-dimethoxy-5-methyl-1,4-benzoquinone (350 mg) which was obtained in Example 3 was treated with sodium hydrosulfite to give 6-(2-hydroxyethyl)-2,3-dimethoxy-5-methylhydroquinone (313 mg). A solution of the hydroquinone (290 mg) in dimethoxyethane (DME, 4 ml) was added dropwise to a suspension of 60% sodium hydride (450 mg) and methyl iodide (2.7 ml) in DME (3 ml) within 90 minutes at 45°–60° C. After cooling, the reaction mixture was treated with diluted hydrochloric acid. The aqueous layer was separated and extracted with ethyl ether. The combined ethereal layer was worked up in the usual manner. The resulting residue (240 mg) was purified by a silica gel column chromatography to give 1,2,3,4-tetramethoxy-5-methyl-6-(2-methoxyethyl)benzene (330 mg). To a solution of this compound (210 mg) in tetrahydrofuran (14 ml), silver (II) oxide (490 mg) and 6N nitric acid (1 ml) were added. After being stirred for 5 minutes at 0° C., silver (II) oxide (2 g) and 6N nitric acid (2 ml) were further added. The reaction mixture was worked up in the usual manner and purified by column chromatography to give 2,3-dimethoxy-5-methyl-6-(2-methoxyethyl)-1,4-benzoquinone as an orange oil. NMR spectrum (δ value in CDCl$_3$): 2.05 (3H, s, CH$_3$ on ring), 2.73 (2H, t, J=6 Hz, CH$_2$ on ring), 3.32 (3H, s, OCH$_3$), 3.47 (2H, t, J=6 Hz, CH$_2$O), 4.00 (6H, s, OCH$_3$ on ring).

Example 5

6-Hydroxymethyl-2,3-dimethoxy-5-methyl-1,4-benzoquinone which was obtained in Example 2 was treated in a manner similar to that of Example 4, and 6-methoxymethyl-2,3-dimethoxy-5-methyl-1,4-benzoquinone was obtained as orange crystals, m.p. 31°–36° C.

Elemental analysis for C$_{11}$H$_{14}$O$_5$: Calcd.: C, 58.40; H, 6.24; Found: C, 58.61; H, 6.11.

NMR spectrum (δ value in CDCl$_3$): 2.08 (3H, s, CH$_3$ on ring), 3.33 (3H, s, OCH$_3$), 3.97 (6H, s, OCH$_3$), 4.28 (2H, s, CH$_2$ on ring).

Reference Example 1

In 50 ml of petroleum ether was dissolved 10.5 g of 11-acetoxyundecanoylchloride. To the solution was added 20 ml of ice-water. To the mixture was further added, while stirring, 4 g of sodium peroxide little by little. The organic layer was separated, and the aqueous layer was subjected to extraction with ether. The organic layer and the ether extracts were combined, washed with water and dried, followed by evaporation of the solvent to yield 8.6 g of white wax-like bis(11-acetoxyundecanoyl)peroxide.

IR spectrum $\nu_{max}^{Nujol}$ cm$^{-1}$: 1820, 1730

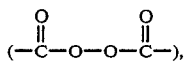

1740 (OCOCH₃).

Reference Example 2

In 2 ml of ether was dissolved 0.41 g of acetylglycolyl. To the solution was added 1 ml of ice-water. To the mixture was added, while stirring 0.41 g of sodium peroxide little by little. The reaction solution was diluted with ice-water, then extracted with ether. The extract was washed with water, dried, and then the ether was evaporated under reduced pressure at 0° C. to yield colorless oily bis(acetoxyacetyl) peroxide.

IR spectrum $\nu_{max}^{CHCl_3}$ cm$^{-1}$: 1820, 1800

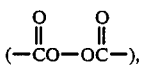

1760 (OCOCH₃).

What is claimed is:

1. A compound of the formula:

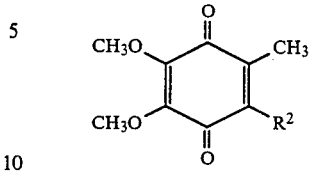

wherein $R^2$ is an alkyl group of 1 to 2 carbon atoms having at its terminal end a hydroxyl group which may be protected by alkyl having 1 to 4 carbon atoms, aliphatic carboxylic acyl having 1 to 4 carbon atoms, aromatic acyl having 7 to 8 carbon atoms or tetrahydropyranyl.

2. A compound as claimed in claim 1, wherein the compound is 6-hydroxymethyl-2,3-dimethoxy-5-methyl-1,4-benzoquinone.

3. A compound as claimed in claim 1, wherein the compound is 6-acetoxymethyl-2,3-dimethoxy-5-methyl-1,4-benzoquinone.

* * * * *